(12) United States Patent
Quam et al.

(10) Patent No.: US 9,370,330 B2
(45) Date of Patent: Jun. 21, 2016

(54) RADIATION FIELD AND DOSE CONTROL

(71) Applicant: Siemens Medical Solutions USA, Inc., Malvern, PA (US)

(72) Inventors: Steve D Quam, Carpentersville, IL (US); Mikhail Uvarov, Hoffman Estates, IL (US); Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 11 days.

(21) Appl. No.: 14/174,264

(22) Filed: Feb. 6, 2014

(65) Prior Publication Data

US 2014/0226794 A1    Aug. 14, 2014

Related U.S. Application Data

(60) Provisional application No. 61/762,345, filed on Feb. 8, 2013.

(51) Int. Cl.
    *A61B 6/06*    (2006.01)
    *G21K 1/04*    (2006.01)
    *G21K 1/10*    (2006.01)
    *A61B 6/00*    (2006.01)

(52) U.S. Cl.
    CPC . *A61B 6/06* (2013.01); *A61B 6/541* (2013.01); *A61B 6/544* (2013.01); *A61B 6/545* (2013.01); *G21K 1/046* (2013.01); *G21K 1/10* (2013.01); *A61B 6/481* (2013.01); *A61B 6/503* (2013.01)

(58) Field of Classification Search
    CPC ........... G21K 1/04; G21K 1/02; G21K 1/046; A61B 6/06; A61B 6/481; A61B 6/503; A61B 6/541; A61B 6/544; A61B 6/545
    USPC ........................................................ 350/150
    See application file for complete search history.

(56) References Cited

U.S. PATENT DOCUMENTS

| | | | |
|---|---|---|---|
| 5,199,438 A | 4/1993 | Pearlman | |
| 5,229,668 A | 7/1993 | Hughes et al. | |
| 5,565,914 A | 10/1996 | Motta | |
| 5,574,765 A | 11/1996 | Hassler et al. | |
| 5,590,649 A | 1/1997 | Caro et al. | |
| 5,778,294 A | 7/1998 | Hiraoka et al. | |
| 5,832,051 A | 11/1998 | Lutz | |
| 5,854,656 A | 12/1998 | Noggle | |
| 5,872,572 A | 2/1999 | Rossignac | |
| 6,061,426 A * | 5/2000 | Linders et al. | 378/149 |
| 6,148,062 A | 11/2000 | Romeas | |
| 6,154,516 A | 11/2000 | Heuscher et al. | |
| 6,256,406 B1 | 7/2001 | Garland et al. | |
| 6,275,560 B1 | 8/2001 | Blake et al. | |
| 6,295,336 B1 | 9/2001 | Aach et al. | |
| 6,393,091 B1 | 5/2002 | Slack et al. | |
| 6,411,740 B1 | 6/2002 | Daly | |
| 6,477,553 B1 | 11/2002 | Druck | |
| 6,487,271 B1 | 11/2002 | Laurent | |
| 6,614,448 B1 | 9/2003 | Garlick et al. | |
| 6,708,052 B1 | 3/2004 | Mao et al. | |

(Continued)

*Primary Examiner* — Glen Kao

(57) ABSTRACT

A system and method includes a matrix of elements, each of the elements comprising a respective radiation-attenuating material providing a respective radiation attenuation profile over a respective area of the matrix, and wherein at least one of the elements is independently-controllable to change its respective radiation attenuation profile over its respective area.

22 Claims, 12 Drawing Sheets

(56) References Cited

U.S. PATENT DOCUMENTS

| | | |
|---|---|---|
| 6,795,526 B2 | 9/2004 | Kump et al. |
| 6,827,489 B2 | 12/2004 | Nicolas et al. |
| 6,873,682 B2 | 3/2005 | Francke et al. |
| 6,993,117 B2 | 1/2006 | Toth et al. |
| 7,031,504 B1 | 4/2006 | Argiro et al. |
| 7,076,029 B2 | 7/2006 | Toth et al. |
| 7,092,490 B2 | 8/2006 | Saladin et al. |
| 7,120,231 B2 | 10/2006 | Spahn |
| 7,142,630 B2 | 11/2006 | Suzuki |
| 7,187,794 B2 | 3/2007 | Liang et al. |
| 7,274,770 B2 | 9/2007 | Nederpelt |
| 7,308,073 B2 | 12/2007 | Tkaczyk et al. |
| 7,336,768 B2 | 2/2008 | Ogawa |
| 7,340,032 B2 | 3/2008 | Besson |
| 7,342,993 B2 | 3/2008 | Besson |
| 7,426,258 B1 | 9/2008 | Zweig |
| 7,434,998 B2 | 10/2008 | Saito |
| 7,526,065 B2 | 4/2009 | Hardesty |
| 7,630,477 B2 | 12/2009 | Toth et al. |
| 7,640,137 B2 | 12/2009 | Numata et al. |
| 7,653,179 B2 | 1/2010 | Ramsauer et al. |
| 7,680,249 B2 | 3/2010 | Yuan |
| 7,747,058 B2 | 6/2010 | Spahn |
| 2002/0126799 A1* | 9/2002 | Saladin et al. ............... 378/152 |
| 2004/0024300 A1* | 2/2004 | Graf ................ A61N 5/1049 600/407 |
| 2004/0105525 A1* | 6/2004 | Short et al. .................. 378/98.8 |
| 2005/0069086 A1 | 3/2005 | Deych et al. |
| 2005/0117707 A1* | 6/2005 | Baier et al. .................... 378/156 |
| 2005/0243970 A1 | 11/2005 | Bernhardt |
| 2006/0182226 A1 | 8/2006 | Yuan et al. |
| 2008/0205597 A1* | 8/2008 | Ono ................................ 378/65 |
| 2008/0267348 A1 | 10/2008 | Puusaari et al. |
| 2008/0272309 A1 | 11/2008 | Schweizer et al. |
| 2009/0122962 A1 | 5/2009 | Gould et al. |
| 2009/0312648 A1 | 12/2009 | Zhang et al. |
| 2010/0056897 A1 | 3/2010 | Zhang |
| 2010/0081917 A1 | 4/2010 | Zhang et al. |
| 2010/0098216 A1 | 4/2010 | Dobson |
| 2010/0111262 A1 | 5/2010 | Lee et al. |
| 2010/0150307 A1 | 6/2010 | Grodzins |
| 2013/0308747 A1* | 11/2013 | Abraham et al. ............... 378/16 |

* cited by examiner

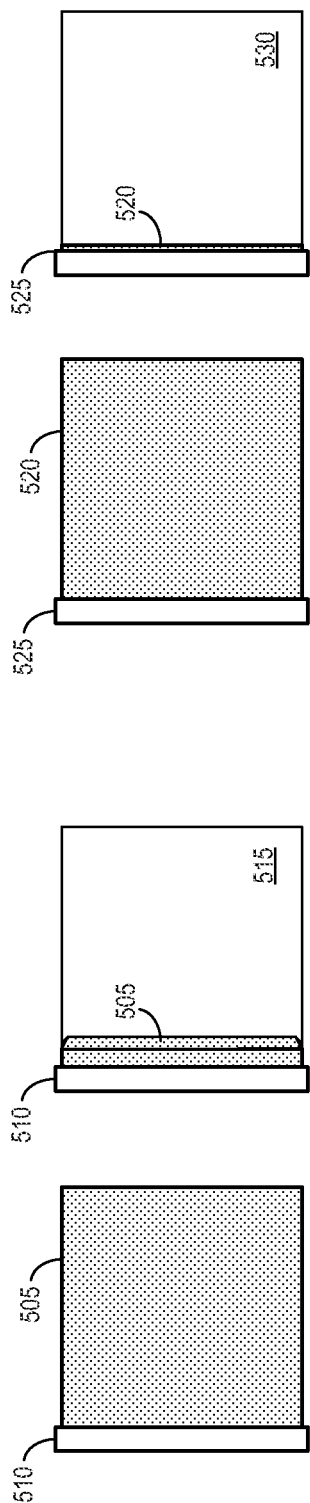
FIG. 5A
FIG. 5B
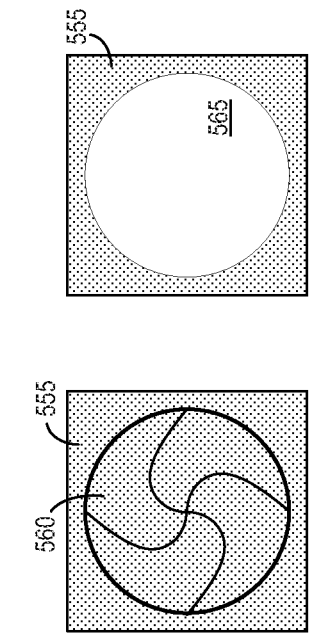
FIG. 5C
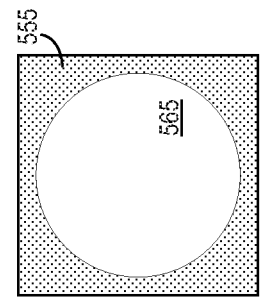
FIG. 5D

RADIATION FIELD AND DOSE CONTROL

CROSS REFERENCE TO RELATED APPLICATIONS

This application claims benefit to and priority of U.S. Patent Application Ser. No. 61/762,345, filed on Feb. 8, 2013, the contents of which are hereby incorporated by reference in their entirety for all purposes.

BACKGROUND

1. Field

The embodiments described below relate to systems to control radiation field shape and/or dose distributions within a radiation field.

2. Description

X-ray imaging is used to acquire images of internal patient volumes. Generally, an x-ray image is formed by emitting x-rays toward a patient volume and detecting the x-rays over an area after they have passed though the patient volume. Intensities of the detected x-rays are converted to pixel intensities over the area. The pixel intensities therefore comprise an image in which materials having different attenuative properties are represented by different pixel intensities. As a result, the image illustrates internal structures through which the x-rays have passed.

In order to minimize the exposure of the patient to x-ray radiation, an imaging plan is typically designed to primarily deliver radiation to a region of interest. The imaging plan specifies an angle at which the x-rays are to be delivered to the patient, as well as a shape of the delivered radiation field. The angle is controlled by rotating an x-ray tube around the patient, and the shape is controlled using a collimator.

A conventional collimator is disposed between the x-ray tube and the patient, and includes two pairs of "jaws" disposed perpendicularly to one another. Each jaw is composed of a set of radiation-blocking "leaves", each of which may be moved linearly into and out of a radiation field emitted by the x-ray tube. The leaves may therefore be controlled to define a rough outer perimeter of a radiation field delivered to the patient.

Known imaging systems may employ electrophysiological signals (e.g., an electrocardiogram (ECG) signal, a blood pressure signal, and/or a respiration signal) to trigger x-ray emission and image acquisition. Such triggering may reduce the influence of patient movement (external and internal) on the acquired images. For example, a conventional system may acquire images at uniform time intervals during a specified signal portion (e.g., Q-wave, S-wave, etc.).

Improved control over radiation field shape and radiation dose is desired.

BRIEF DESCRIPTION OF THE DRAWINGS

FIGS. 5A through 5D illustrate changing an attenuation profile of an element according to some embodiments;

DETAILED DESCRIPTION

The following description is provided to enable any person in the art to make and use the described embodiments and sets forth the best mode contemplated for carrying out the described embodiments. Various modifications, however, will remain readily apparent to those in the art.

Figure 1:
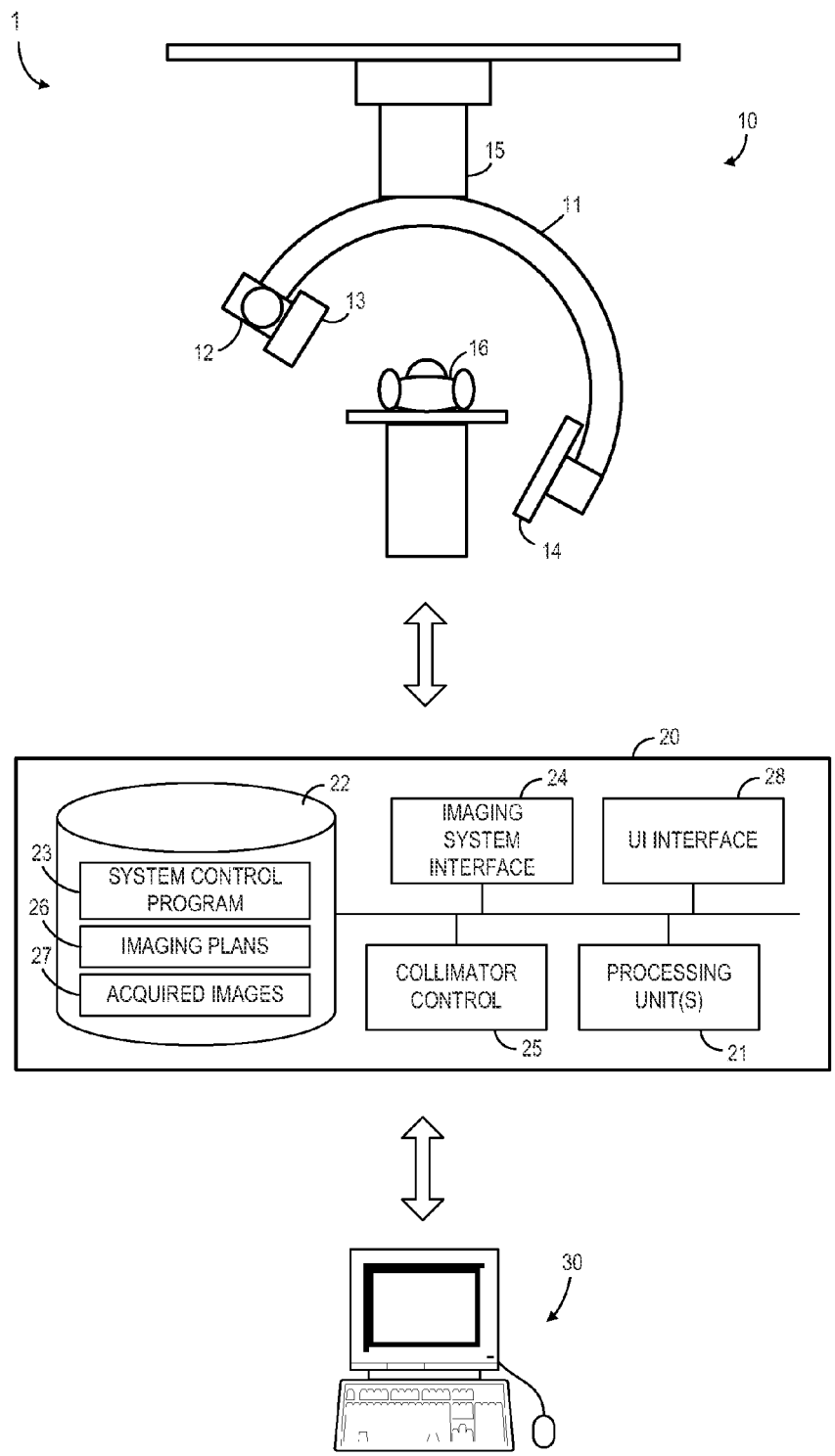
FIG. 1 illustrates a system according to some embodiments.

FIG. 1 illustrates system 1 according to some embodiments. System 1 includes imaging system 10, control system 20, and operator terminal 30. Generally, and according to some embodiments, imaging system 10 acquires images of a patient volume under control of control system 20. An image acquired by imaging system 10 includes one or more data values for each pixel of the image. Control system 20 receives the acquired images and may output the images to terminal 30 for display thereby.

According to the illustrated embodiment, imaging system 10 comprises C-arm 11 on which x-ray radiation source 12, collimator 13 and radiation detector 14 are mounted. C-arm 11 is mounted on support 15 and is configured to translate clockwise or counter-clockwise with respect to support 15. This translation rotates radiation source 12, collimator 13 and radiation detector 14 around a central volume while maintaining the physical relationship therebetween.

Embodiments are not limited to C-arm-based x-ray imaging systems. Imaging system 10 may comprise any system for acquiring images that is or becomes known. According to some embodiments, imaging system 10 may comprise an x-ray imaging system, a camera, a magnetic resonance imaging system, a positron emission tomography scanner, or a computed tomography imaging system.

Radiation source 12 may comprise any suitable radiation source, including but not limited to an x-ray tube. In some embodiments, radiation source 12 emits electron, photon or other type of radiation having energies ranging from 50 to 150 keV.

According to some embodiments, collimator 13 selectively blocks and/or filters radiation emitted from radiation source 12. Collimator 13 may thereby define the shape of a radiation field which reaches patient 16. Moreover, according to some embodiments, collimator 13 may attenuate, but not block, radiation in one or more regions of the radiation field so that an intensity of the radiation field received by patient 16 is heterogeneous across its area.

Collimator 13 may be controlled according to an imaging plan to create a particular radiation field shape and/or dose profile for imaging. A dose profile describes the spatial distribution of radiation intensities within a radiation field. For example, an imaging plan may specify a dose profile in which regions of a radiation field corresponding to radiation-sensitive patient structures exhibit a lower intensity than other regions of the radiation field.

Collimator 13 may consist of a matrix of elements, with each element comprising a respective radiation-attenuating material. The radiation-attenuating material of an element provides a particular radiation attenuation profile over the area of the matrix associated with the element. At least one of the elements is independently-controllable to change its respective radiation attenuation profile over its respective area. Examples of collimator 13 in accordance with some embodiments will be described below with respect to FIGS. 2 through 7.

Radiation detector 14 may comprise any system to acquire an image based on received x-ray radiation. In some embodiments, radiation detector 14 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In some embodiments, radiation detector 14 converts received photons to electrical charge without requiring a scintillator layer. The photons are absorbed directly by an array of amorphous selenium photoconductors. The photoconductors convert the photons directly to stored electrical charge. Radiation detector 14 may comprise a CCD or tube-based camera, including a light-proof housing within which are disposed a scintillator, a mirror, and a camera.

The charge developed and stored by radiation detector 14 represents radiation intensities at each location of a radiation field produced by x-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 14 may therefore represent a two-dimensional projection image of these tissues.

Some embodiments may also comprise a contrast injector (not shown) to controllably introduce contrast medium into a patient volume. In this regard, structures (e.g., blood vessels) which contain contrast medium appear darker in x-ray images than they would otherwise appear.

System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processing units 21 may execute system control program 23 to move C-arm 11, to cause radiation source 12 to emit radiation, to control collimator 13 to change the radiation attenuation profile of one or more of its elements, to control detector 14 to acquire an image, and to perform any other function. In this regard, system 20 includes imaging system interface 24 and collimator control 25 for controlling the elements of system 10.

One or more processing units 21 may execute system control program 23 to control imaging system 10 based on one or more of imaging plans 26. Imaging plans 26 may specify a projection angle, an intensity of emitted radiation, a radiation field shape and profile, and other parameters for acquiring an image. In some embodiments which will be described below, the intensity of emitted radiation and/or radiation field shape and profile specified by a treatment plan vary over time and/or are gated based on one or more physiological signals.

Images acquired from system 10 may be stored in data storage device 22 as acquired images 27, in DICOM or another data format. Each acquired image 27 may be further associated with details of its acquisition, including but not limited to imaging plane position and angle, imaging position, radiation source-to-detector distance, patient anatomy imaged, patient position, contrast medium bolus injection profile, x-ray tube voltage, collimator configuration, image resolution and radiation dosage.

Acquired images 27 may be provided to terminal 30 via UI interface 28 of system 20. UI interface 28 may also receive input from terminal 30, which may be used to control collimator 13 and other elements of imaging system 10 for the acquisition of images.

Terminal 30 may simply comprise a display device and an input device coupled to system 20. In some embodiments, terminal 30 is a separate computing device such as, but not limited to, a desktop computer, a laptop computer, a tablet computer, and a smartphone.

According to some embodiments, systems 10 and 20 form a closed-loop system for execution of an imaging plan 26. For example, system 20 controls radiation source 12 and collimator 13 to generate a radiation field of a shape and intensity profile required by an imaging plan 26, detector 14 acquires an image of the radiation field as attenuated by patient 16, system 20 analyzes the image to determine whether the generated radiation field conforms to the imaging plan 26 and, if not, system 20 determines a correction and controls the elements of collimator 13 (and, perhaps, radiation source 12) to apply the correction.

Each of system 10, system 20 and terminal 30 may include other elements which are necessary for the operation thereof, as well as additional elements for providing functions other than those described herein.

Figure 2:
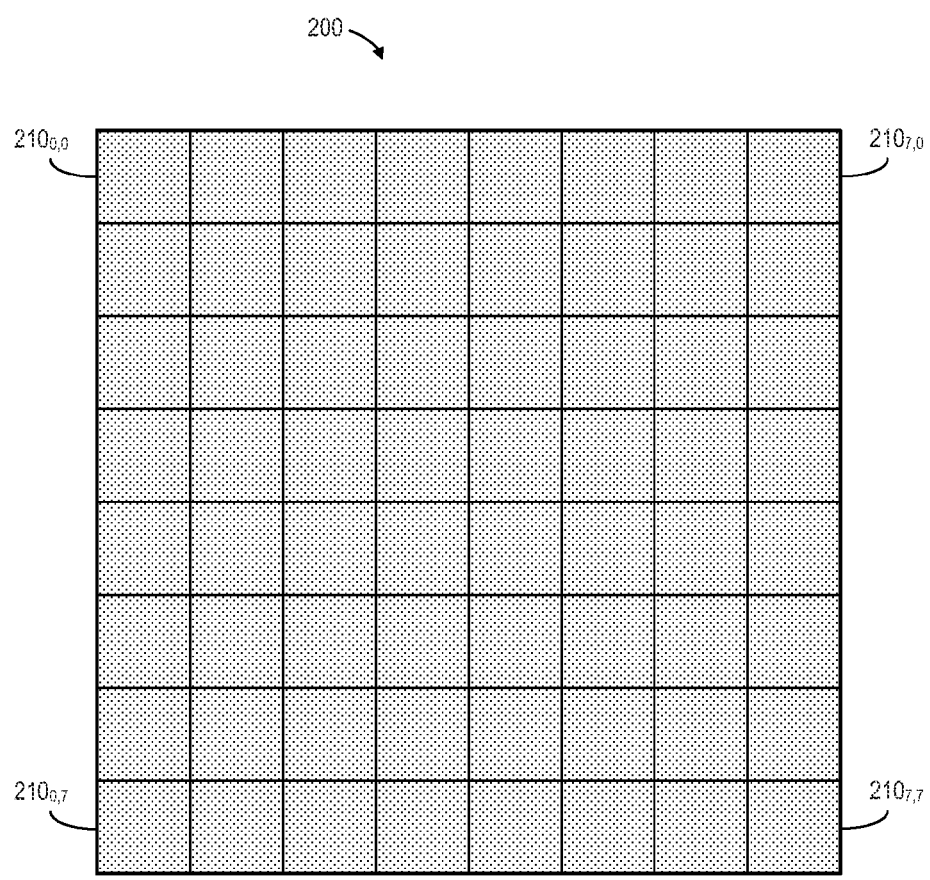
FIG. 2 is a view of a matrix of elements according to some embodiments.

FIG. 2 illustrates collimator 200 according to some embodiments. Collimator 13 of FIG. 1 may be an implementation of collimator 200. Collimator 200 comprises a matrix of M×N elements 210, where, in the illustrated example, M=8=N. Each of elements 210 comprises a radiation-attenuating material providing a respective radiation attenuation profile over a respective area of the matrix. For example, element $210_{0,0}$ attenuates radiation in a particular manner over the area of the matrix occupied by element $210_{0,0}$. This attenuation profile is provided by the material of which element $210_{0,0}$ consists, as well as by the thickness of the material.

According to some embodiments, the material is lead. Any other suitable radiation-attenuating materials may be utilized in conjunction with some embodiments, including compounds of more than one material.

At least one of elements 210 is controllable independent from the other elements 210 to change its respective radiation profile over its respective area. Such control may include moving an element at least partially out of its area, so that radiation may pass at least partially unimpeded. In some embodiments, an element may be controlled to change an attenuation coefficient of its radiation-attenuation material. This change may be effected by applying an electrical potential to the material, heating or cooling the material, draining fluid from or introducing fluid into the material, or by any other system that is or becomes known.

Figure 3:
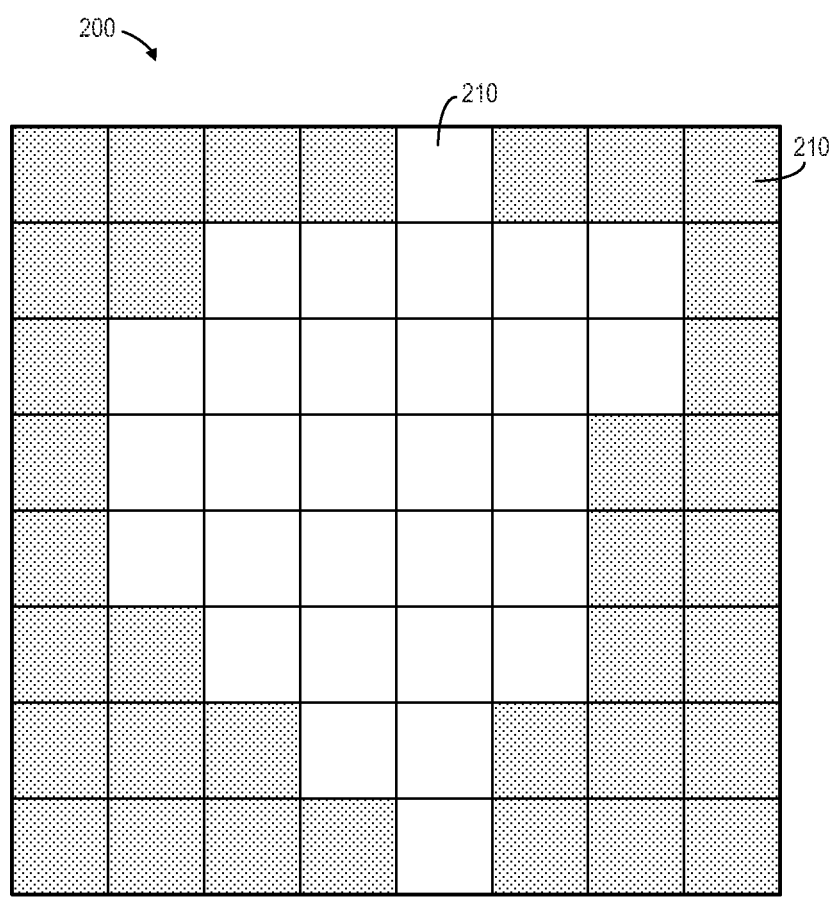
FIG. 3 is a view of a matrix of elements according to some embodiments.

FIG. 3 depicts changes of radiation profiles of several elements 210 of collimator 200 according to some embodiments. Lighter-colored elements 210 are assumed to have been "opened" or otherwise configured to allow radiation to pass through their respective areas. According to one example of the illustrated embodiment, darker-colored elements 210 block radiation from passing. Therefore, as configured in FIG. 3, collimator 200 creates a radiation field in the shape of the lighter-colored elements 210 for delivery to a patient.

Figure 4:
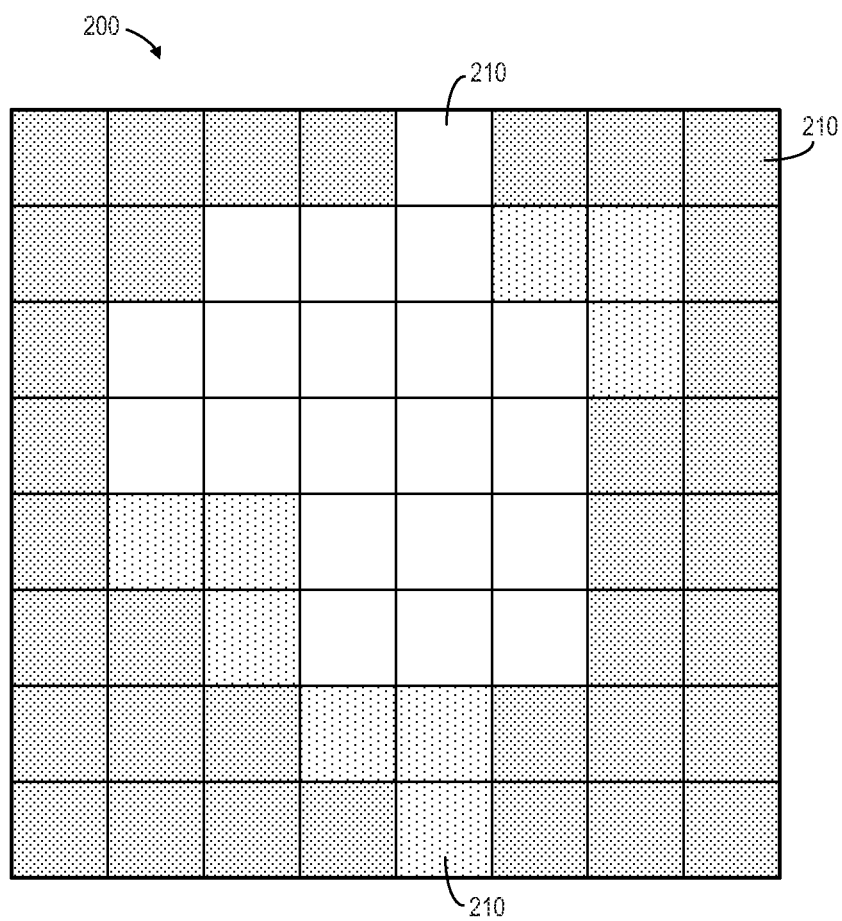
FIG. 4 is a view of a matrix of elements according to some embodiments.

FIG. 4 illustrates collimator 200 in which elements 210 exhibit three different radiation attenuation profiles. Embodiments are therefore not limited to any particular number of radiation attenuation profiles within a single matrix of elements.

FIGS. 5A through 5D illustrate several mechanisms for changing a radiation attenuation profile of an element according to some embodiments. FIG. 5A shows a door-like arrangement in which radiation-attenuating material 505 rotates on hinge 510 to swing out from the plan of the page. The resulting unoccupied area 515 allows radiation to pass therethrough unattenuated.

Hinge 510 may include a turning/rotating control unit. The turning angle (and therefore the radiation attenuation profile of the element) may be changed by incremental degrees, such as 0, 15, 30, 45, 60, 75, 90 degrees, using a stepping micromotor. According to some embodiments, the thickness of material 505 is 0.2-1 mm and the size of the element is 1×1 mm to 5×5 mm. The turning angle for the may be adaptively and automatically manipulated in real time.

FIG. 5B depicts an element in which material 520 retracts into portion 525, leaving area 530 for passage of unattenuated radiation. Any suitable mechanical arrangement may be utilized to support this function. For example, material 520 may roll onto a spool within portion 525, or may fold in an accordion-like manner into portion 525.

According to the element of FIG. 5C, material 535 rotates on pivot 540, thus allowing radiation to pass through areas 545 and 550. Lastly, the element of FIG. 5D includes frame 555 and blades 560 covering area 565. Blades 560 may be controlled to retract into frame 555 to expose area 565. Any of areas 515, 530, 545, 550 and 565 may include respective radiation-attenuating material.

The elements of FIGS. 5A through 5B may also utilize micro-motors to control their radiation attenuation profiles, in response to programmed instruction for each image acquisition. Element states may be changed in parallel or serially by transmitting control signals from a control system (e.g., system 20) to a collimator control unit. Each set of control signals may be decoded for control of a corresponding step motor to manipulate the angle and window opening size, which limits and modulates the x-ray emission energy and dose delivered to a patient.

Although each element of FIGS. 2-5D is illustrated as a square, elements may exhibit any shape according to some embodiments. Moreover, elements of a same collimator may exhibit different shapes. Elements 210 may be mounted in any suitable housing which provides any electrical and/or mechanical hardware required for operation thereof.

Figure 6:
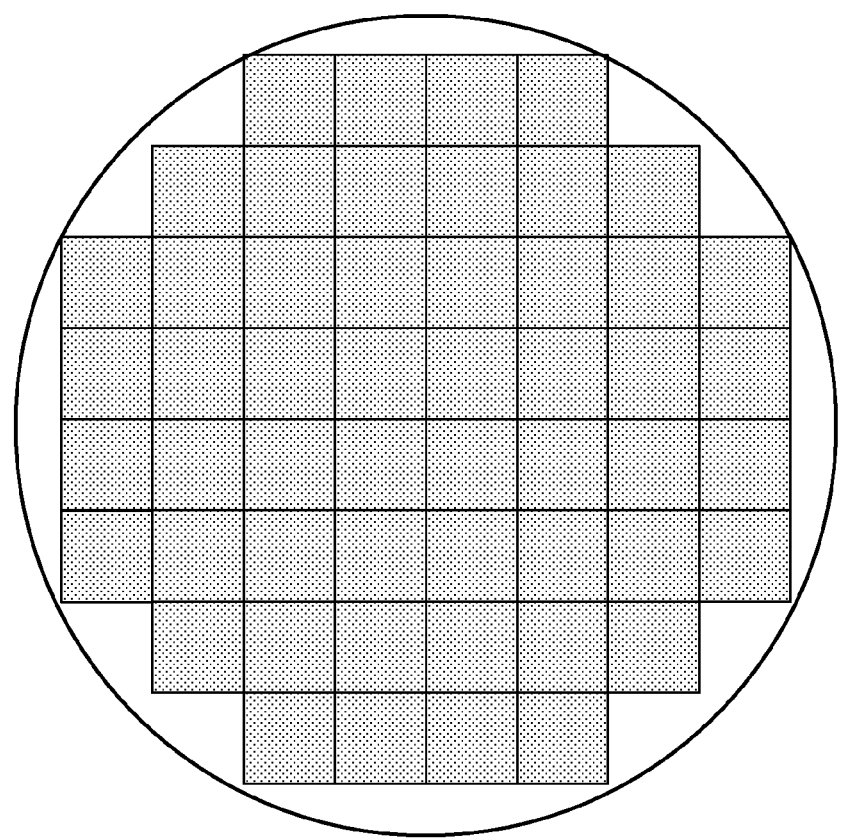
FIG. 6 is a view of a matrix of elements according to some embodiments.

Elements 210 of FIGS. 2-4 are arranged in a square matrix, but embodiments are not limited thereto. For example, FIG. 6 illustrates a non-square matrix of elements according to some embodiments. Generally, the term matrix is used herein to describe any arrangement of elements into a shape in which one or more elements are disposed between elements located on the perimeter of the shape.

Figure 7:
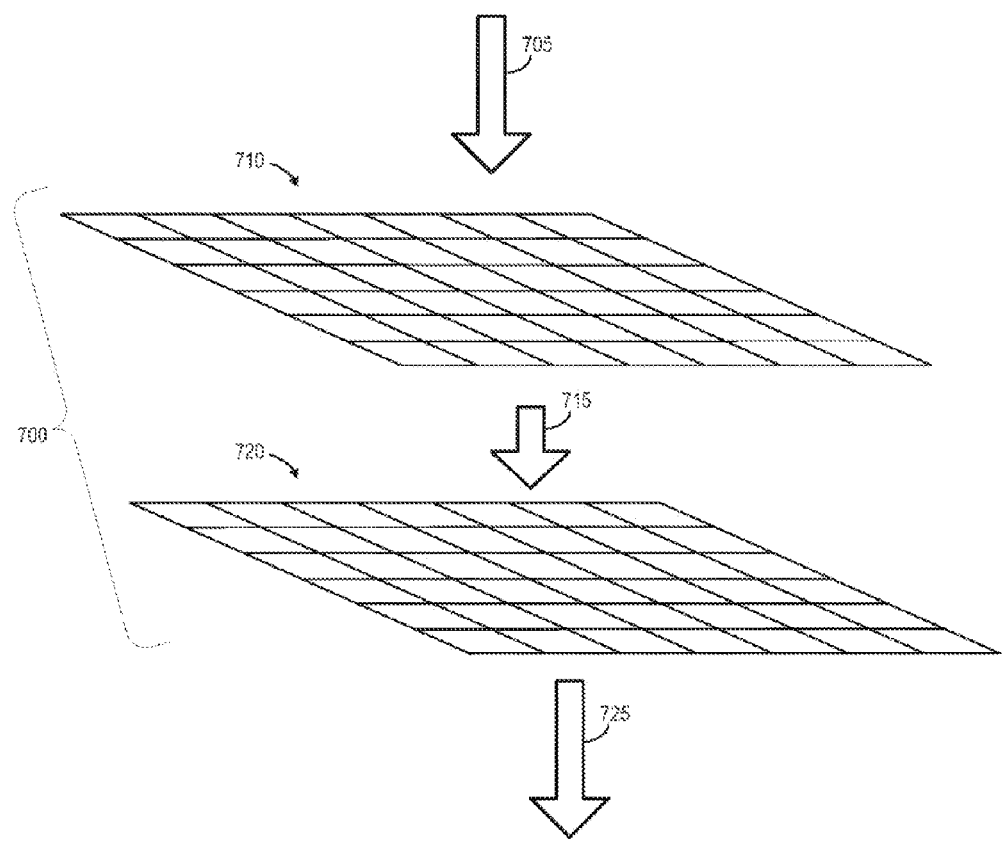
FIG. 7 illustrates radiation attenuation via layers of matrices according to some embodiments.

FIG. 7 illustrates collimator 700 including matrices 710 and 720 according to some embodiments. Collimator 700 is shown in an exploded view and without a supporting housing or electrical and mechanical hardware in order to illustrate the positions of matrices 710 and 720 relative to one another. Each of matrices 710 and 720 is a matrix of elements, with each element of each matrix comprising a respective radiation-attenuating material providing a respective radiation attenuation profile over its respective area. By employing two matrices, some embodiments provide finer control over a total radiation attenuation profile (i.e., an attenuation profile measured as the difference between radiation entering a collimator and radiation leaving the collimator).

FIG. 7 illustrates radiation 705 emitted by a radiation emitting device (not shown). Radiation 705 intercepts matrix 710 over an area of matrix 710. Elements of matrix 710 which lie within the area then attenuate radiation 705 according to the radiation-attenuating profiles of their radiation-attenuating materials, resulting in attenuated radiation 715. Similarly, radiation 715 intercepts matrix 720 over an area of matrix 720, and elements of matrix 720 which lie within this area attenuate radiation 715 according to the radiation-attenuating profiles of their radiation-attenuating materials. Radiation 725 emerges from matrix 720 and continues toward the volume to be imaged.

Embodiments may include three or more matrices. Each matrix of a collimator according to some embodiments may exhibit a different shape. The materials of each matrix may differ, and each matrix may implement a different system for controlling its elements to change their respective radiation-attenuating properties. An imaging plan may specify a radiation attenuation profile for each element of each matrix of a multi-matrix collimator or, according to some embodiments, the imaging plan may specify a desired overall attenuation profile. In the latter case, a control system of the collimator controls the elements of each matrix to change their radiation attenuation profiles in accordance with the desired overall attenuation profile.

Figure 8:
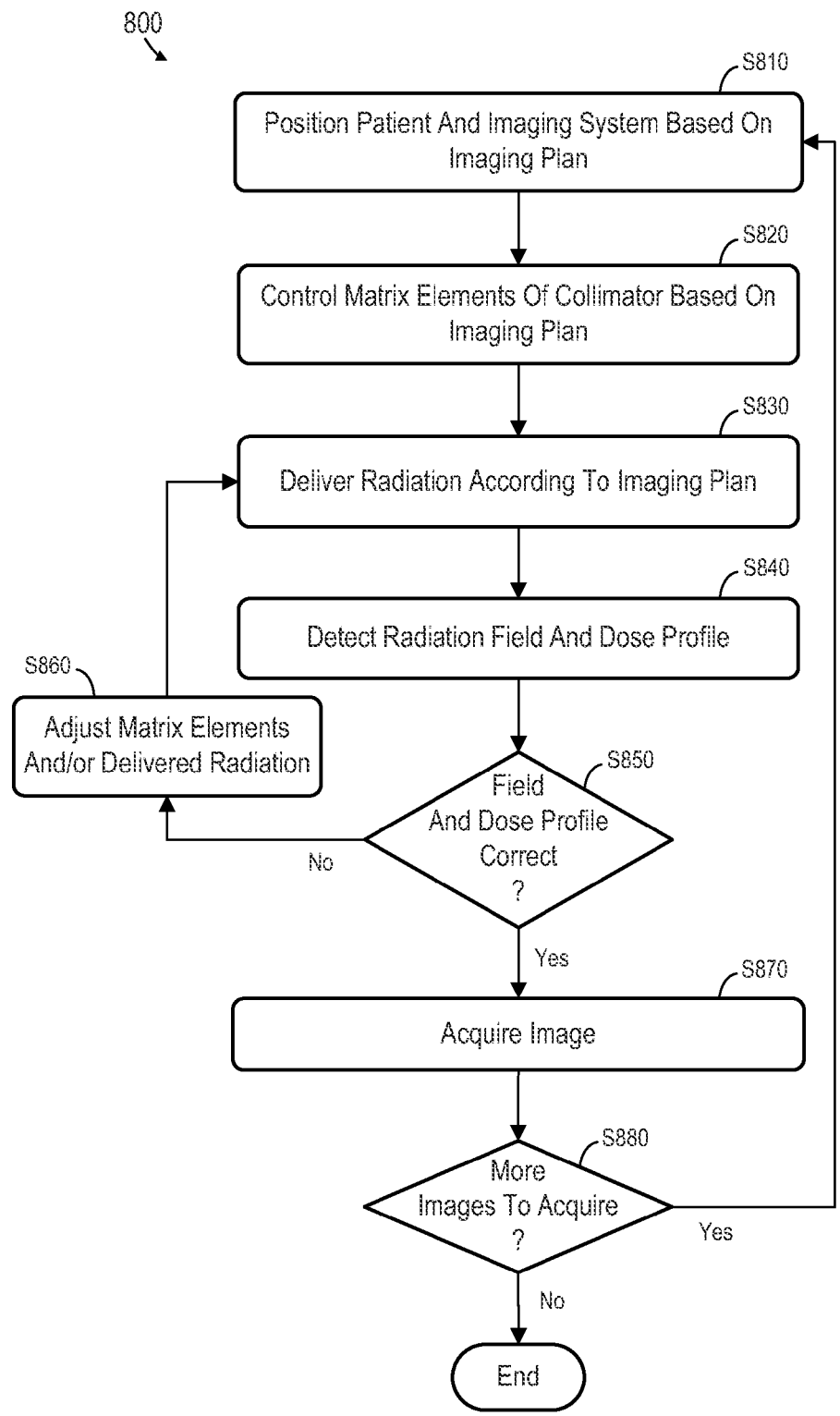
FIG. 8 is a flow diagram of a process according to some embodiments.

FIG. 8 is a flow diagram of process 800 according to some embodiments. Process 800 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape.

Initially, at S810, a patient and an imaging system are positioned according to an imaging plan. The patient and the imaging system are positioned such that an image of a region of interest may be acquired at a desired projection angle. Such positioning may be performed manually and/or automatically via execution of an imaging plan by a system control program. Positioning at S810 may include movement of the patient, a table supporting the patient, an image acquisition device (e.g., a detector panel), and/or a radiation-emitting device (e.g., by moving a gantry or other moveable support to which the radiation-emitting device is attached).

Next, at S820, matrix elements of a collimator are controlled according to the imaging plan. The elements are controlled to change their radiation attenuation profiles so that a radiation field having a desired radiation profile is delivered to the patient. The control may therefore depend on the radiation field which is expected to be received by the collimator from the radiation-emitting device. Therefore, in order to achieve a desired radiation field, the imaging plan may specify parameters of radiation to be emitted by the radiation-emitting device and radiation attenuation profiles of the collimator elements.

Figure 9:
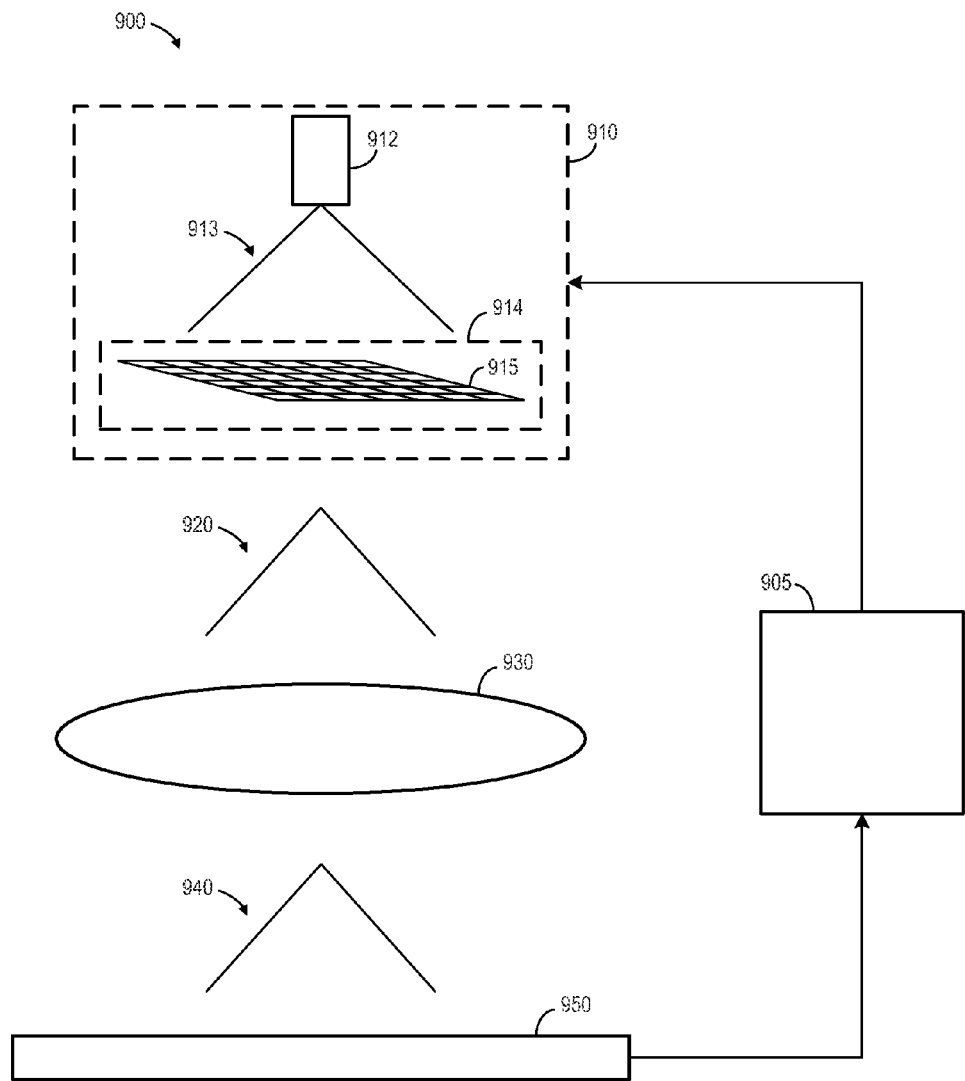
FIG. 9 illustrates imaging control according to some embodiments.

Radiation is delivered according to the imaging plan at S830, and a radiation field and dose profile are detected at S840. FIG. 9 illustrates system 900 for explaining aspects of process 800 according to some embodiments.

Control unit 905 controls imaging head 910 at S820 and S830. Imaging head 910 includes radiation-emitting device 912 (e.g., an x-ray tube) and collimator 914 including matrix of elements 915 according to some embodiments. Accordingly, control unit 905 controls the elements of matrix 915 based on an imaging plan at S820 and controls radiation-emitting device 912 (e.g., an x-ray tube) to deliver radiation 913 according to the plan at S830.

Collimator 914 attenuates radiation 913 to produce radiation 920. Radiation 920 passes through body 930 and is attenuated thereby to produce radiation 940, which is consequently detected by detector 950.

Returning to process 800, it is determined at S850 whether the field and dose profile detected by detector 950 are correct. For example, control unit 905 may compare the field and dose profile with a field and dose profile which are expected by the imaging plan. If the field/dose profile are not sufficiently similar to the expected/desired field or profile, the elements of matrix 915 and/or the radiation delivered by device 912 are adjusted at S860. Flow then returns to S830 and continues as described above until the determination at S850 is affirmative.

In some embodiments, S810 through S860 are initially performed without the presence of body 930. This calibration mode may provide better assurance that the radiation emitted from imaging head 910 exhibits a desired profile/dose.

Flow continues to S870 after an affirmative determination at S850. An image is acquired at S870. The acquired image may simply be the most-recently detected field/profile at S840 (i.e., in a case that body 930 was positioned according to the imaging plan), or may be acquired by positioning body 930, controlling radiation-emitting device 912 to deliver radiation, and detecting the resulting radiation 940.

At S880, it is determined whether more images are to be acquired. If not, process 800 terminates. If so, flow returns to S810 and continues as described above. For example, creation of a three-dimensional reconstruction of a patient volume requires the acquisition of images from multiple projection angles. In such a case, flow returns to S810 to position the patient and imaging system according to a next projection angle.

Figure 10:
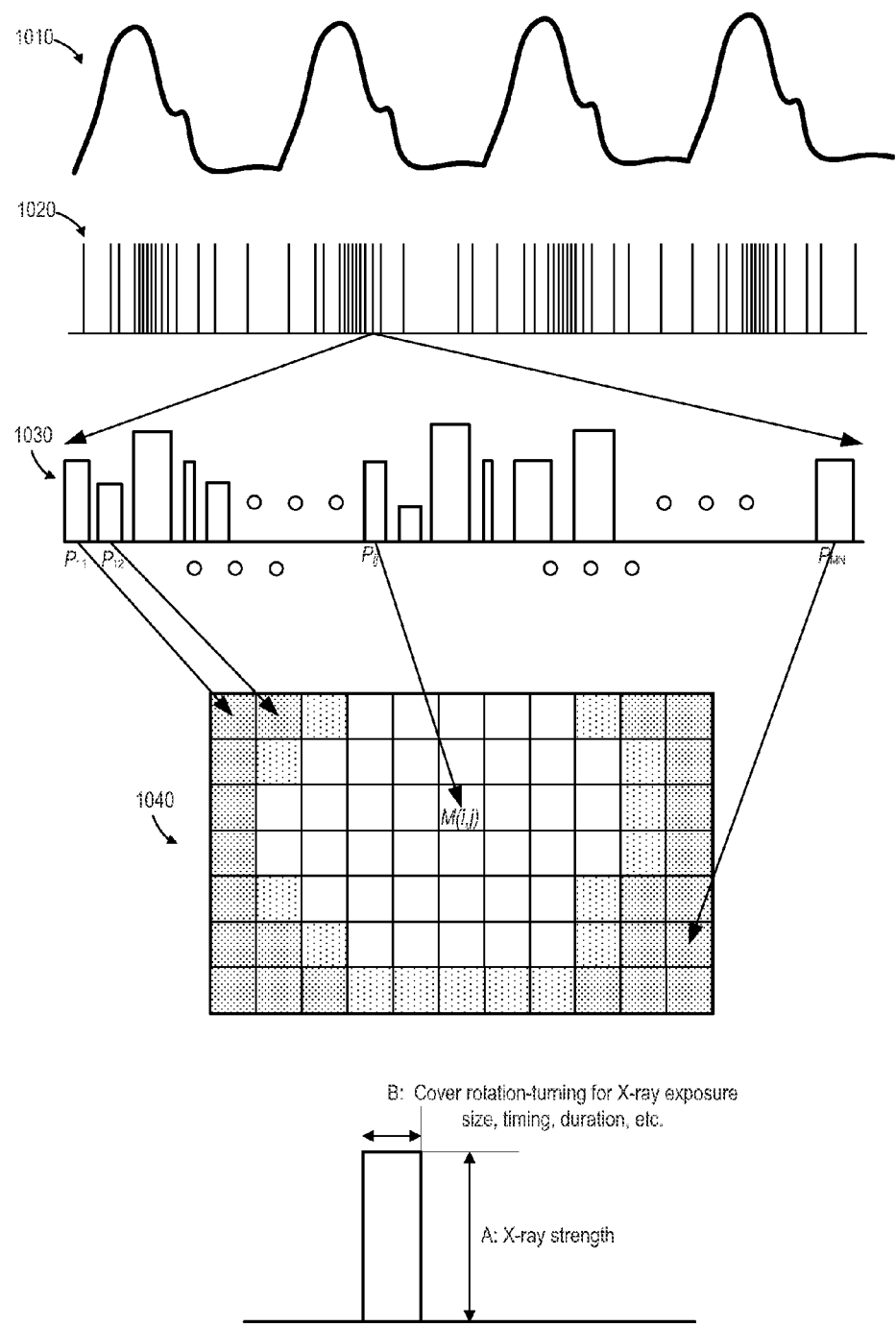
FIG. 10 illustrates gating-based control of a matrix of elements according to some embodiments.

FIG. 10 illustrates collimator control based on according to some embodiments. The process illustrated in FIG. 10 may comprise an implementation of process 800 described above. Signal 1010 is a blood pressure signal which is used to gate x-ray emission and control of collimator elements for image acquisition in the present example. Waveform 1020 illustrates timing of x-ray emissions with respect to signal 1010, and signals 1030 illustrates control signals for each element of matrix 1040 during a single x-ray emission.

It will be assumed that the FIG. 10 illustrates acquisition of cardiac images. Each vertical line of waveform 1020 corresponds to acquisition of an image, therefore waveform 1020 shows that the frequency of image acquisition increases during periods of increased heart motion.

Signals 1030 specify control of each of elements $P_{MN}$ of matrix 1040 during one image acquisition. According to the present example, a height of an element-specific signal corresponds to an x-ray strength to be passed by the element, while the width of the element-specific signal may correspond to angle of rotation of the element cover, size, timing, duration, etc. Control over elements $P_{MN}$ of matrix 1040 may be nonlinear and non-uniform. Control may be determined based on heart size and/or function by controlling dose and the cell cover turn angle control parameter. This nonlinear and non-uniform control may be programmed and quantized by the system such that each element is controlled independently of other elements.

Control may be based on human experience (such as of a doctor, nurse, etc.) and/or imaging system control software. The control may specify x-ray dose, energy, area size exposed, element rotation angle. For linear element control, calculations based on linear parameters may be used, such as energy-amplitude frequency, statistical parameter (probability, entropy, Gaussian distribution). For nonlinear methods, expert system control, fuzzy modeling control or artificial neural network (ANN) control may be used to change element attenuation profiles based on a pre-scanned image and prior knowledge of the imaging system and a patient anatomical area to be imaged.

Figure 11:
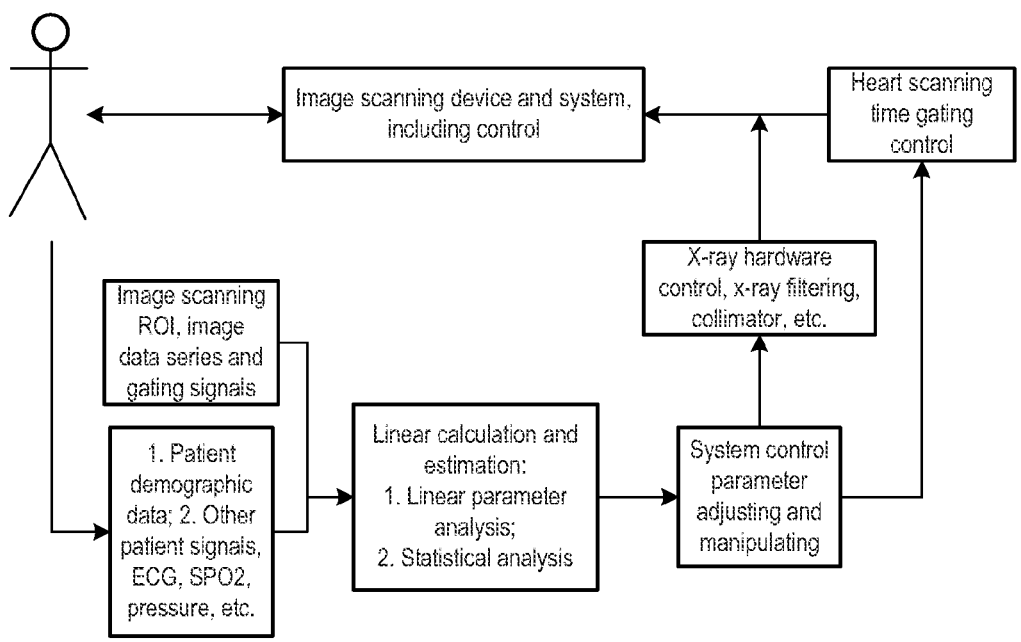
FIG. 11 illustrates linear-based image acquisition according to some embodiments.

FIG. 11 illustrates linear-based image acquisition according to some embodiments (e.g., linear patient parameters calculation, statistical parameter calculation). Patient data (including, for example, patient demographic data, recording data, SPO2, ECG, and patient heart scanning image data) is processed by linear methods, such as frequency analysis, energy calculation, spectral analysis, and statistical parameters calculation. Steps include recording patient real time data and pre-scanning an image, linear method-based diagnosis based on the data; spatial and time parameter adjustment including matrix element shape, edge, angle, and turn on-off timing, and communication of gating and control signals to an image scanning system for each image acquisition. Control further includes specifying x-ray C-arm rotation speed, image resolution and acquisition triggering for images of a series.

Control parameters may be linked to a linear output index. For example, if a matrix element is determined to be in an image area, the angle of the radiation-attenuating material of the element is set to 90 degrees (i.e., fully open). If a matrix element is determined to not be in an image area, the angle of the radiation-attenuating material of the element is set to 0 degrees (i.e., closed). Elements located along an edge of the image area are set to a 45 degree angle (i.e., half open).

Figure 12:
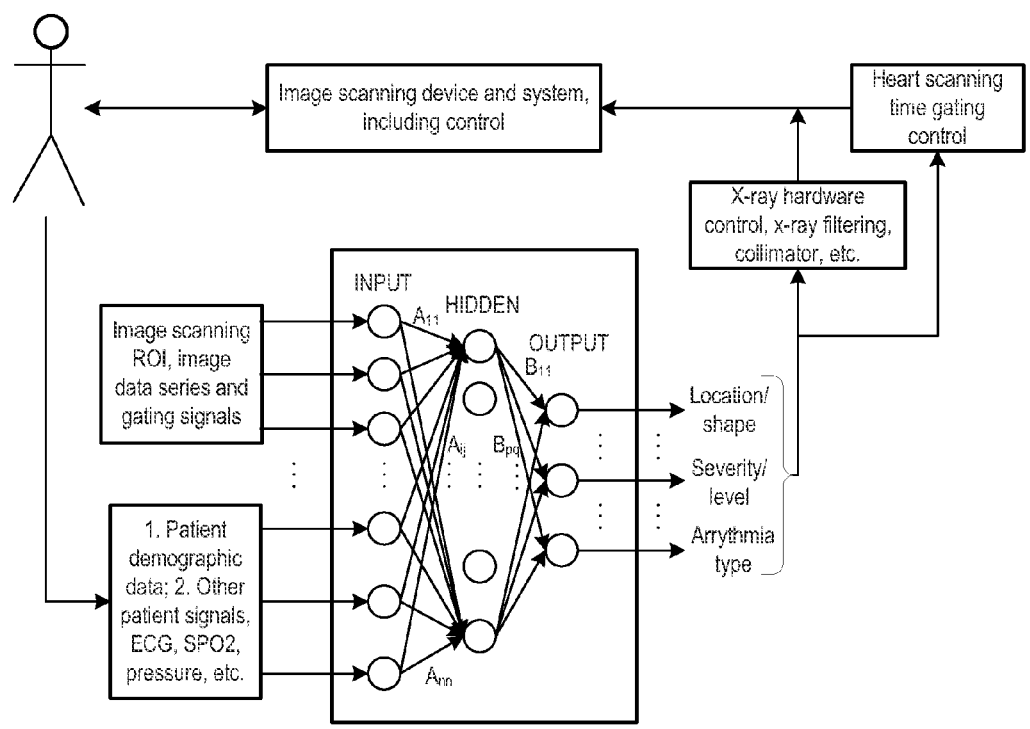
FIG. 12 illustrates non-linear-based image acquisition according to some embodiments.

FIG. 12 illustrates a non-linear system (e.g., an ANN control system) in which collimator elements and time gating parameters are adjusted continuously in real time. The illustrated ANN structure includes three layers: input layer, hidden layer and output layer. $A_{ij}$ and $B_{pq}$ are weights between the inputs and the calculation index, which can be adaptively adjusted and tuned using a training data set. The ANN system provides self-learning ability based on new input data (e.g., patient recording hemodynamic data, electrophysiological data, and patient vital signs signals), which may increase the accuracy and precision of the calculated results. Patient signal analysis results from recorded patient data, and patient history are used to calculate control of collimator elements as described herein. The control steps for the non-linear system are similar to those in the FIG. 11 system.

Those in the art will appreciate that various adaptations and modifications of the above-described embodiments can be configured without departing from the scope and spirit of the claims. Therefore, it is to be understood that the claims may be practiced other than as specifically described herein.

What is claimed is:
1. A system comprising:
an x-ray radiation collimator comprising:
a matrix of elements, each of the elements comprising a respective x-ray radiation-attenuating material providing a respective x-ray radiation attenuation profile over a respective area of the matrix, and
wherein at least one of the elements is independently-controllable by control signals to change its respective x-ray radiation attenuation profile over its respec- tive area, wherein the control signals are generated based on an imaging plan and gated by blood pressure signals.

2. The system according to claim 1, wherein at least one of the elements is independently-controllable to change its respective x-ray radiation attenuation profile over its respective area by moving at least a portion of its x-ray radiation-attenuating material.

3. The system according to claim 2, wherein the at least one of the elements that is independently-controllable connects to the matrix by a hinge, wherein the x-ray radiation-attenuating material rotates on the hinge to swing away from a plane of the matrix and wherein the angle at which the element swings by the hinge from the plane of the matrix effects the respective x-ray radiation attenuation profile.

4. The system according to claim 2, wherein the at least one of the elements that is independently-controllable connects to the matrix by a spool, wherein the radiation-attenuating material rolls on or off of the spool and wherein the amount of which the element rolls on or off the spool affects the respective x-ray radiation attenuation profile.

5. The system according to claim 1, wherein at least one of the elements is independently-controllable to change its respective x-ray radiation attenuation profile over its respective area by changing an attenuation coefficient of its x-ray radiation-attenuating material.

6. The system according to claim 5, wherein the changing of the attenuation coefficient is effected by at least one of:
applying an electrical potential to the x-ray radiation-attenuating material; and
heating or cooling the x-ray radiation-attenuating material.

7. The system according to claim 1, the x-ray radiation collimator further comprising:
a second matrix of elements, where each of the second matrix of elements comprises a respective x-ray radiation-attenuating material providing a respective x-ray radiation attenuation profile over a respective area of the second matrix, and
wherein at least one of the second matrix of elements is independently-controllable to change its respective x-ray radiation attenuation profile over its respective area.

8. The system according to claim 7, wherein at least one of the second matrix of elements is independently-controllable to change its respective x-ray radiation attenuation profile over its respective area by changing an attenuation coefficient of its x-ray radiation-attenuating material.

9. The system according to claim 7, the x-ray radiation collimator further comprising:
a third matrix of elements, where each of the third matrix of elements comprises a respective x-ray radiation-attenuating material providing a respective x-ray radiation attenuation profile over a respective area of the third matrix, and
wherein at least one of the third matrix of elements is independently-controllable to change its respective x-ray radiation attenuation profile over its respective area.

10. The system according to claim 9, wherein at least one of the second matrix of elements and at least one of the third matrix of elements is independently-controllable to change its respective x-ray radiation attenuation profile over its respective area by changing an attenuation coefficient of its x-ray radiation-attenuating material.

11. The system according to claim 7, wherein the planes of the first matrix and the second matrix are located parallel to one another.

12. The system according to claim 1, further comprising:
an x-ray radiation emitting device to emit x-ray radiation toward the x-ray radiation collimator,
wherein at least one of the matrix of elements is independently-controllable to change its respective x-ray radiation attenuation profile over its respective area by moving at least a portion of its x-ray radiation-attenuating material such that a portion of the emitted x-ray radiation may pass through at least a portion of its area without being attenuated by the x-ray radiation-attenuating material.

13. The system according to claim 12, further comprising:
an x-ray radiation detector to detect x-ray radiation attenuated by one or more of the elements of the x-ray radiation collimator; and
a processor to determine whether the detected x-ray radiation conforms to an x-ray radiation profile and, in a case that the detected x-ray radiation does not conform to the x-ray radiation profile, to control one or more of the elements to change the x-ray radiation attenuation profile of the one or more of the elements over their respective areas.

14. A method comprising:
controlling, via control signals, at least one of a matrix of elements of an x-ray radiation collimator to change a respective x-ray radiation attenuation profile of the at least one of the matrix of elements over a respective area of the matrix, wherein each of the elements comprises a respective x-ray radiation-attenuating material providing a respective x-ray radiation attenuation profile over its respective area; and
generating the control signals based on an imaging plan, wherein the control signals are gated by blood pressure signals.

15. The method according to claim 14, further comprising controlling at least one of the elements to change its respective x-ray radiation attenuation profile over its respective area by moving at least a portion of its x-ray radiation-attenuating material.

16. The method according to claim 14, further comprising controlling at least one of the elements to change its respective x-ray radiation attenuation profile over its respective area by changing an attenuation coefficient of its x-ray radiation-attenuating material.

17. The method according to claim 14, further comprising:
controlling at least one of a second matrix of elements of the x-ray radiation collimator to change a respective x-ray radiation attenuation profile of the at least one of the second matrix of elements over a respective area of the second matrix,
wherein each of the second matrix of elements comprises a respective x-ray radiation-attenuating material providing a respective x-ray radiation attenuation profile over its respective area.

18. The method according to claim 17, further comprising controlling at least one of the elements to change its respective x-ray radiation attenuation profile over its respective area by changing an attenuation coefficient of its x-ray radiation-attenuating material.

19. The method according to claim 17, further comprising:
controlling at least one of a third matrix of elements to change a respective x-ray radiation attenuation profile of the at least one of the third matrix of elements over a respective area of the matrix, wherein each of the third matrix of elements comprises a respective x-ray radiation-attenuating material providing a respective x-ray radiation attenuation profile over its respective area.

20. The method according to claim 19, further comprising controlling at least one of the second matrix of elements and at least one of the third matrix of elements to change its respective x-ray radiation attenuation profile over its respective area by changing an attenuation coefficient of its x-ray radiation-attenuating material.

21. The method according to claim 14, further comprising:
  emitting x-ray radiation toward the radiation collimator; and
  controlling at least one of the matrix of elements to change its respective radiation attenuation profile over its respective area by moving at least a portion of its x-ray radiation-attenuating material such that a portion of the emitted x-ray radiation may pass through at least a portion of its area without being attenuated by the x-ray radiation-attenuating material.

22. The method according to claim 21, further comprising:
  detecting x-ray radiation attenuated by one or more of the elements of the x-ray radiation collimator;
  determining whether the detected x-ray radiation conforms to a x-ray radiation profile; and
  in a case that the detected x-ray radiation does not conform to the x-ray radiation profile, controlling one or more of the elements to change the x-ray radiation attenuation profile of the one or more of the elements over their respective areas.

* * * * *